(12) United States Patent
Zhu

(10) Patent No.: US 6,936,017 B2
(45) Date of Patent: Aug. 30, 2005

(54) APPARATUS FOR TREATING DISEASES OF HUMAN BEINGS

(76) Inventor: Xiaoyi Zhu, Floor 18, International S&T Building, Shennanzhonglu, Shenzhen, Guangdong Province (CN), 518033

( * ) Notice: Subject to any disclaimer, the term of this patent is extended or adjusted under 35 U.S.C. 154(b) by 304 days.

(21) Appl. No.: 10/175,258

(22) Filed: Jun. 18, 2002

(65) Prior Publication Data

US 2002/0193727 A1 Dec. 19, 2002

(30) Foreign Application Priority Data

Jun. 18, 2001 (CN) .................................... 01 1 29428 A

(51) Int. Cl.$^7$ ............................................. A61H 23/02
(52) U.S. Cl. ...................... 601/6; 601/7; 601/9; 601/16
(58) Field of Search ............................ 601/6, 7, 9, 10, 601/15, 16; 604/315

(56) References Cited

U.S. PATENT DOCUMENTS

| 816,748 | A | * | 4/1906 | Saighman | 601/7 |
| 2,655,145 | A | * | 10/1953 | Heger | 601/7 |
| 2,825,102 | A | * | 3/1958 | Hicks | 422/4 |
| 3,315,665 | A | * | 4/1967 | MacLeod | 601/7 |
| 3,516,411 | A | * | 6/1970 | Adler | 601/7 |
| 3,794,035 | A | * | 2/1974 | Brenner | 604/315 |
| 4,428,368 | A | * | 1/1984 | Torii | 601/9 |

FOREIGN PATENT DOCUMENTS

GB 4160 * of 1909 .................... 601/6

* cited by examiner

*Primary Examiner*—Danton DeMille
(74) *Attorney, Agent, or Firm*—Thorpe North & Western, LLP

(57) ABSTRACT

This invention provides apparatus for performing a combination of compensating and sucking chi. Generally, the device includes a housing having an inlet and an outlet; a first treating member connected to the inlet of the housing, having a terminal opening and a plurality of holes in the housing close to the terminal opening. The device further includes a second treating member having a heating device connected to the outlet of the housing; and an air pump arranged in the housing to communicate the outlet with the inlet. The invention also provides an apparatus with a plurality of first treating members and second treating members. With the apparatus of the invention, a vacuum can be formed in the first treating member by driving the pump when the first treating member is contacted with and covers a location of the patient's body.

6 Claims, 5 Drawing Sheets

APPARATUS FOR TREATING DISEASES OF HUMAN BEINGS

PRIORITY DATA

This application claims benefit of Chinese Patent Application No. 01129428.0 filed on Jun. 18, 2001.

FIELD OF THE INVENTION

The present invention relates to an apparatus for treating diseases of a patient, particularly to an apparatus capable of performing the compensation of chi and the suction of chi in respect of a specific location of a patient, on the basis of the traditional Chinese medical theory "combination of compensating chi and sucking chi".

BACKGROUND OF THE INVENTION

Various devices for treating diseases have been developed on the basis of traditional Chinese medical theory, such as cupping and infrared radiating devices. These devices have respective features and are able of producing advantageous effects in treating diseases. According to traditional Chinese medical theory, illness is a result of an imbalance in the universal life force known as "Chi," which is believed to be in a constant state of flux. However, no devices have yet been developed to carry out or perform a traditional Chinese idea for re-balancing Chi, known as "combination of compensating chi and sucking chi". Within the state of flux, there are two polar opposites called YIN and YANG, which are symbolized by the well known gracefully divided circle showing how together they represent the whole being. Compensating chi and sucking chi is used for the purposes of balancing the flux.

SUMMARY OF THE INVENTION

The inventor has developed an apparatus for treating diseases of humans by carrying out the balancing of yin and yang in combination with compensating Chi and sucking Chi with modern physical curing means.

Therefore, an object of the invention is to provide an apparatus for treating diseases of a patient by re-balancing the patient's chi. The apparatus includes a housing comprising an inlet and an outlet, a first treating member connected to the inlet of the housing, with a terminal opening, and having a plurality of holes close to the terminal opening; a second treating member with a heating device connected to the outlet of the housing; and an air pump arranged in the housing to communicate the outlet with the inlet. With the apparatus of the invention, a vacuum can be formed in the first treating member by driving the pump when the first treating member is contacted onto a location of the patient's body.

Another object of the invention is to provide an apparatus for treating diseases of a patient, which includes an inlet and an outlet; at least two first treating members connected to the inlet of the housing, each inlet member including a terminal opening and a plurality of holes close to the terminal opening; at least two second treating members connected to the outlet of the housing, each including a heating device; and an air pump arranged in the housing to communicate the outlet with the inlet. With such an apparatus of the invention, a vacuum can be formed in all of the first treating members by driving the pump when the first treating members contact different locations of the patient's body.

Yet another object of the invention is to provide an apparatus for performing the traditional Chinese medicinal procedure of realigning or re-balancing chi, such as by the method of compensating chi and sucking chi.

In the invention, the inlet is preferably arranged at a side of the housing opposite to the outlet. The second treating member may include a casing. In this case, the heating device may be an infrared lamp disposed in the casing or an electricity-heating film coated on the inner surface of the casing.

In one preferred embodiment of the invention, the second treating member includes a casing, a lining attached to the casing, and a heating device of electricity-heating wires wound in grooves on the outside of the lining. The lining is preferably made of a ceramic material which has at least one element selected from Fe, Zn, Cu, Cr, Mn, Co, In and Mo. In addition, a medical infrared coating may be coated on the inner surface of the lining.

In the invention, the first treating member is preferably shaped like a trumpet, and has a body made of rigid material with a terminal opening made of a flexible material attached to the body. In this manner, the terminal opening of the first treating member can conform to the shape of a patient's body when the first treating member is in contact with and covers the selected portion of the patient's body.

The bottom portion of the first treating member is connected to the inlet of the housing through a first connecting tube. Since a plurality of holes close to the terminal opening are disposed through the body of the first treating member, when the pump is driven, air in the first treating member will be sucked off and a vacuum is formed therein. Meanwhile, air out of the first treating member will be sucked therein through the holes. When the pump operates, air out of the first treating member flows into the holes so quickly that the skin covered by the first treating member feels stimulated by the flowing air.

The apparatus according to the invention preferably comprises a controller for controlling the operation of the pump and the temperature of the heating device. With the controller, it is possible to adjust the vacuum degree of the first treating member as well as the temperature of the air in the second treating member.

DETAILED DESCRIPTION OF PREFERRED EMBODIMENTS

The above purposes and the advantageous effects of the invention are further illustrated by reference to the following description of preferred embodiments of the invention in connection with the drawings.

Figure 1:
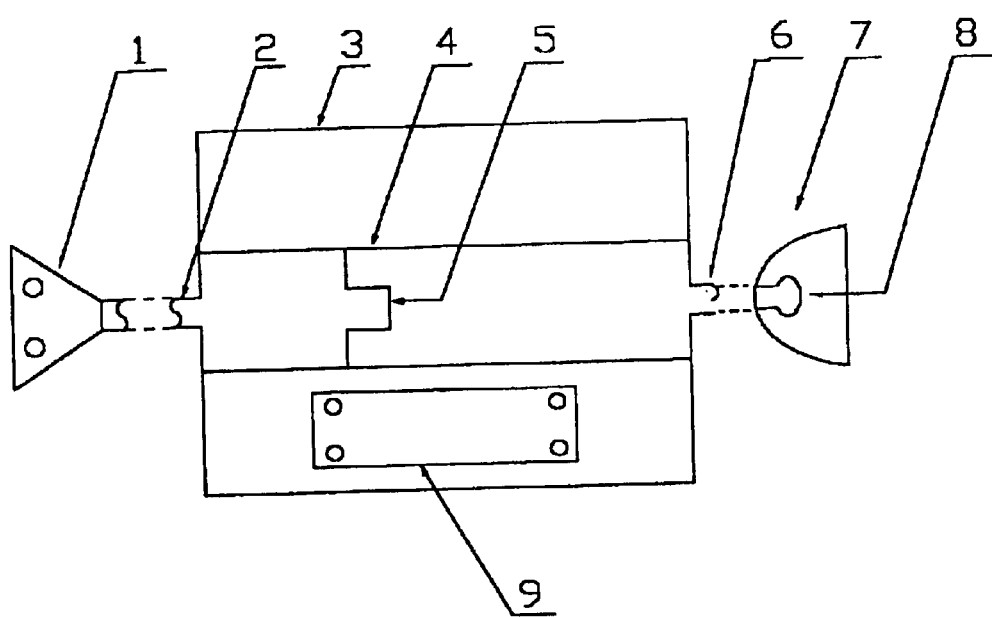
FIG. 1 schematically illustrates an apparatus according to one embodiment of the invention.

FIG. 1 schematically shows the structure of an apparatus of treating diseases of a patient according to the present invention. The apparatus comprises a housing 3, an air pump 5, a first treating member 1 and a second treating member 7. The housing is connected to the first treating member 1 through a first connecting tube 2, and to the second treating member 7 through a second connecting tube 6. Reference numeral 4 is included to illustrate a channel connected to both the first and second connecting tubes. As shown in FIG. 1, the second treating member 7 may include a heating device 8. Reference numeral 9 represents a control circuit for controlling the pump and heating device.

Figure 2:
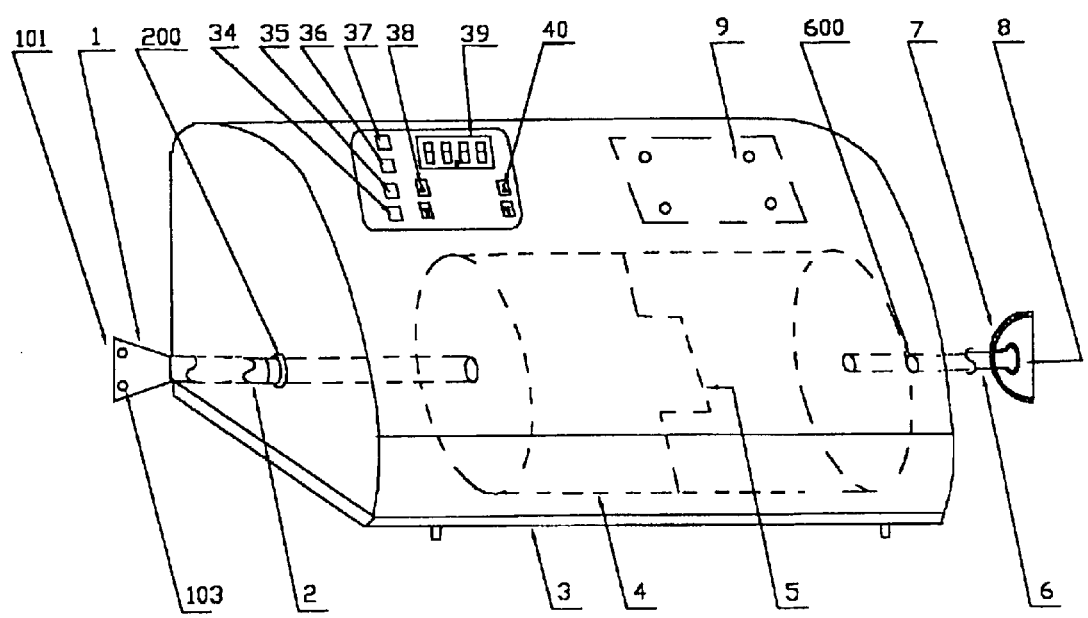
FIG. 2 is a perspective view of an apparatus according to one embodiment of the invention.

Referring to FIG. 2, is shown an apparatus of one embodiment of the invention. The first treating member 1 is shaped as a trumpet and includes a terminal opening 101 and a plurality of holes 103 close to the terminal opening 101. An inlet 200 is connected to the first treating member 1 through the first connecting tube 2, and an outlet 600 is connected to the second treating member 7 through the second connecting tube 6. A control panel is set on the housing 3. The panel connected to the control circuit 9 includes several buttons 34, 35, 36, 37, 38 and 40 and a time indicator 39. With the panel, the vacuum degree in the air channel 5, and the temperature in the second treating member can be adjusted, as will be recognized by those of ordinary skill in the art.

Figure 3:
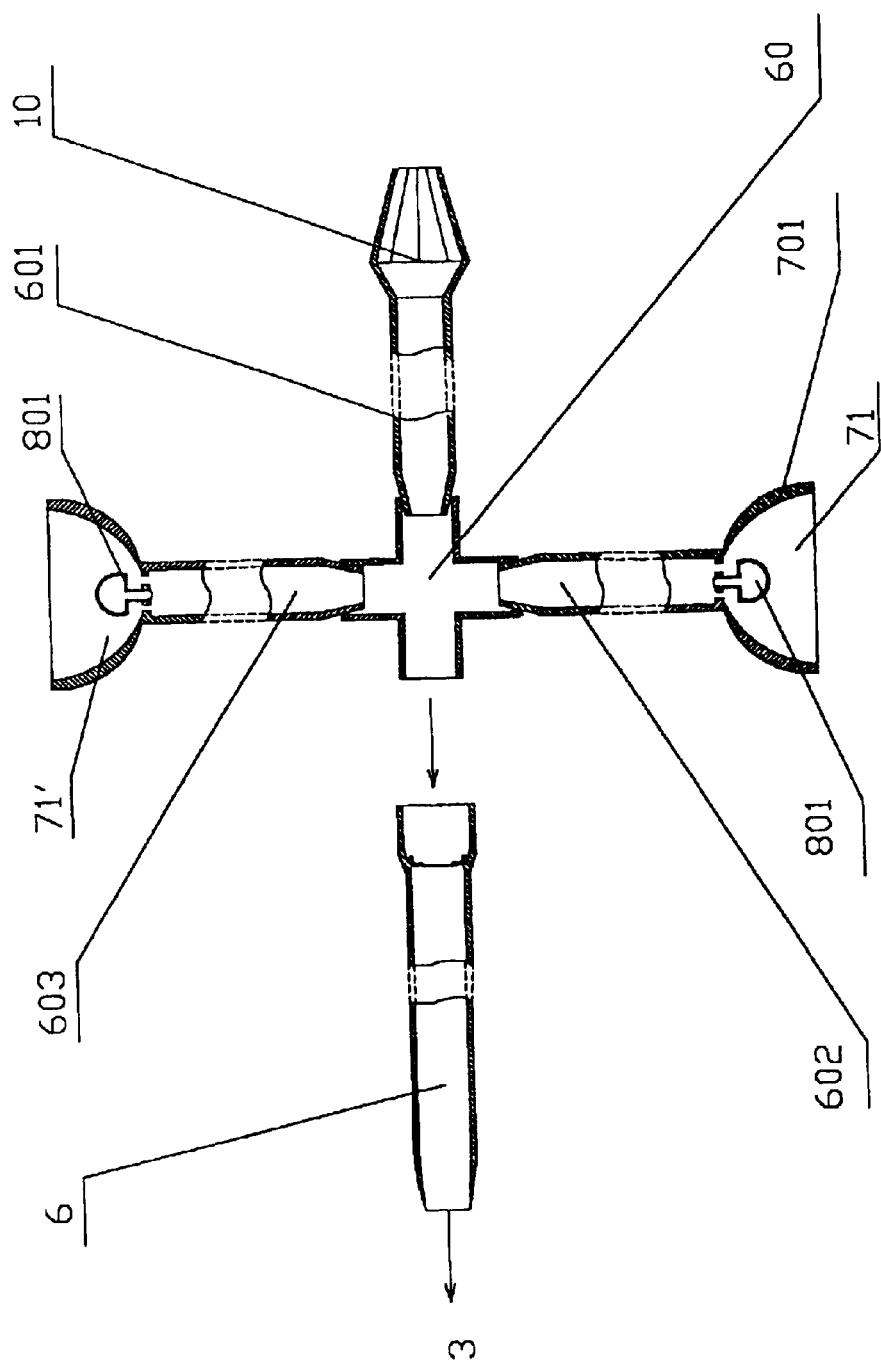
FIG. 3 shows a schematic view comprising a plurality of second treating members according to the invention.

FIG. 3 shows an embodiment of the second treating member of the invention. In this embodiment, there are three second treating members 10, 71 and 71'. Second treating members 71 and 71' include a casing 701 and an infrared lamp 801. The three second treating members are connected to the second connecting tube 6 via a four-way pipe or junction 60. Reference numerals 601, 602 and 603 are tubes respectively connecting the second treating members 10, 71 and 71' with the four-way pipe 60.

Figure 4:
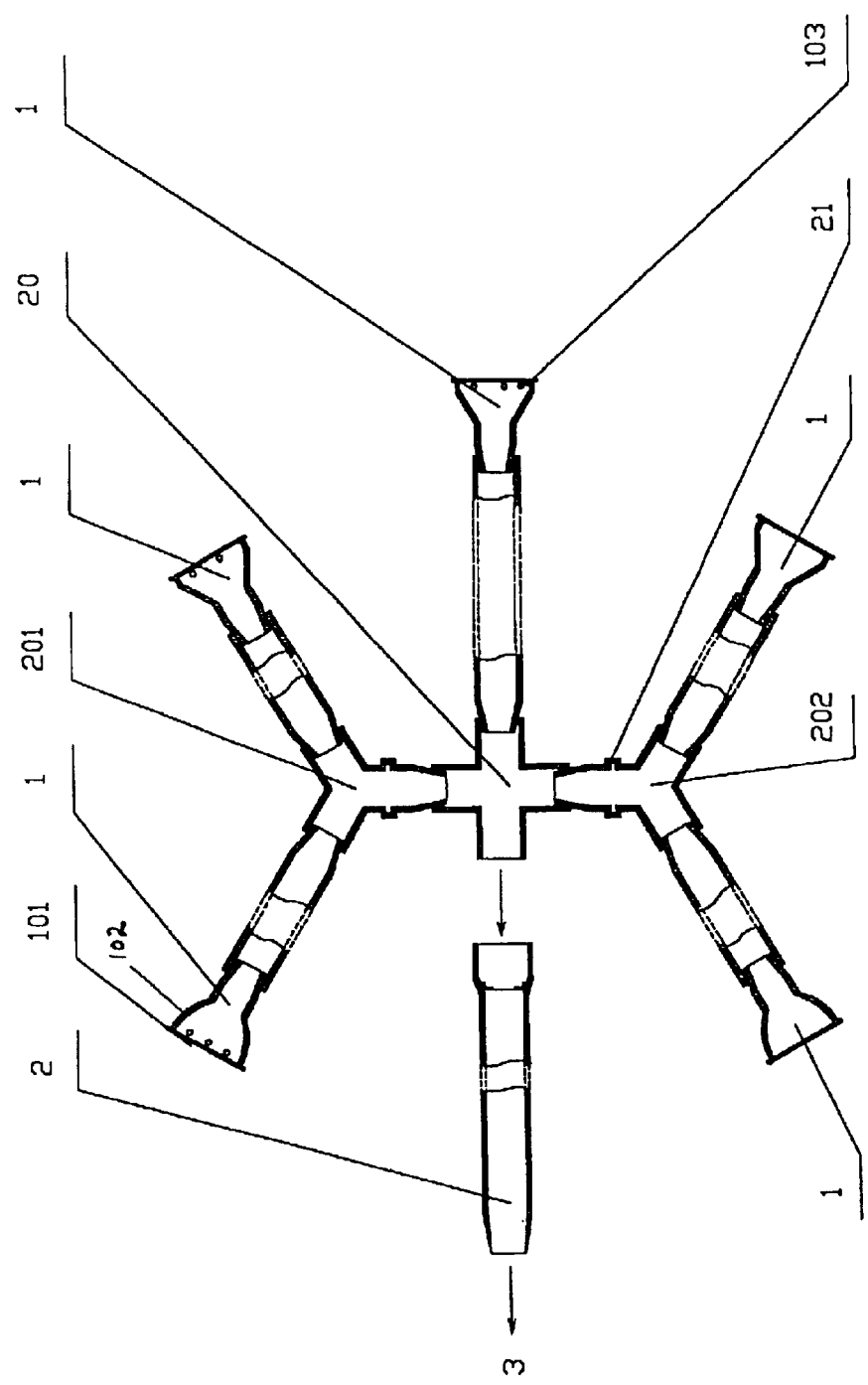
FIG. 4 shows a schematic view comprising a plurality of first treating members according to the invention.

Referring to FIG. 4, five first treating members are connected to the first connecting tube 2 via a four-way pipe 20. In this embodiment, two three-way pipes 201 and 202 are used to connect four second treating members to the four-way pipe. A switch 21 can control the three-way pipes. The first treating member has a casing 102 and a terminal opening 101 attached thereto. The casing 102 may be made of rigid materials such as steel, and hard plastics, and the terminal opening 101 is preferably made from flexible materials such as rubber, so that when the pump works, the casing is not deformed and the terminal opening 101 can closely attach to the patient's body. Also, when the pump is driven, air in the first treating member is sucked off and a vacuum is formed. Therefore, the Chi in the patient's body is sucked out to achieve the purpose of "suction of Chi". Meanwhile, since a plurality of small holes 103 close to the terminal opening 101 are set, air will quickly flow from the outside of the first treating member 1 into the inner of the same. The skin of the patient covered by the first treating member will feel stimulated by air flowing. The quicker the pump rotates, the stronger the skin feels stimulated. The stimulation will make pores in the skin of the patient open so as to improve the effect of suction CHI.

Figure 5:
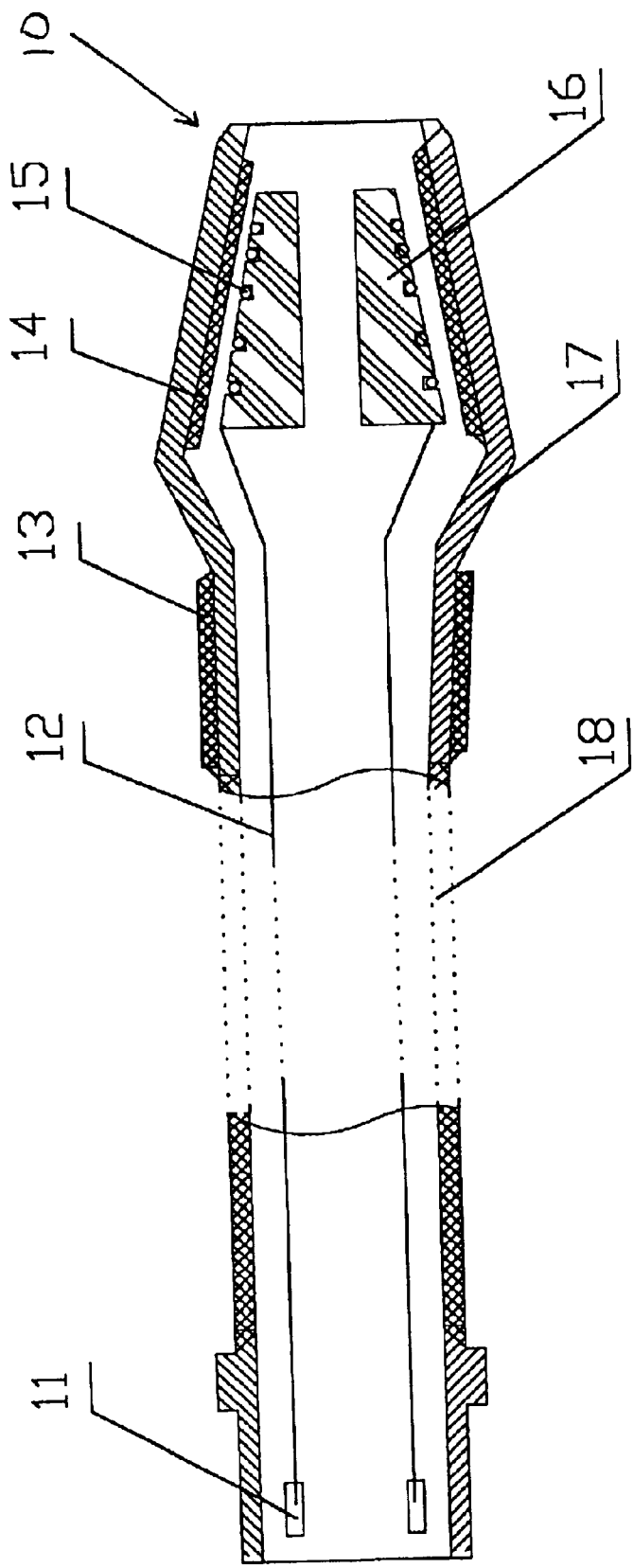
FIG. 5 is a perspective view of a second treating member according to one embodiment of the invention.

Now referring to FIG. 5, is shown a sectional view of the second treating member 10. The second treating member 10 comprises a casing 17, a ceramic lining 16 and an insulating layer 14. An electricity-heating wire 15 is disposed in grooves around the lining 16. A soft tube 18 is used to connect the second treating member 10 to and outlet (not shown). In this FIG. reference numeral 12 represents a cable and reference numeral 11 represents a contact connected to a control circuit (not shown). When the wire 15 is powered, the lining will be heated firstly. Air through the second treating member will subsequently be heated. When the second treating member is moved to close the body, the heated airflow will heat the patient's body so as to achieve the compensation of Chi. A medical infrared coating (not shown) may be coated on the inner surface of the lining. It is known that the infrared ray will help treat the diseases of the patient. In the invention, one or more trace elements like Fe, Zn, Cu, Cr, Mn, Co, In, Mo may be involved in the lining. Heating the lining will result in radiating infrared rays with a different wavelength. Therefore, the apparatus of the invention will significantly improve the effects of the treatment in combination of the radiation of the infrared ray with the compensation of Chi.

The traditional Chinese medical theory not only emphasizes the compensation of Chi and the suction of Chi, but also focuses on the degree of compensating CHI and sucking CHI. In view of a specific location of a patient's body and the condition of the patient, the controller in used the invention may be designed to adjust both the rotation of the pump and the temperature of the airflow for the patient.

The apparatus of treating diseases of the patient in the invention is operated as follows. First, the second treating member is moved to contacted against a specific location of the patient's body. When the air pump is driven, air flows into the first treating member and out of the second treating member. The heating device heats the airflow and the heated air from the second treating member will flow toward the body. Then, the second treating member is removed and the first treating member is contacted against and covers the same location. A vacuum is produced in the first treating member so as to suck Chi from the body. Due to the existence of the holes on the wall of the first treating member, the pump will suck the air outside of it into the inner through the holes to generate airflow. The airflow will result in a stimulation to the skin covered by the first treating member. The stimulation renders pores in the skin open so that the effect of the suction and the compensation of Chi will be significantly improved.

What is claimed is:

1. An apparatus for treating diseases of a patient, comprising
   a housing having an inlet and an outlet;
   a first treating member connected to said inlet, said first treating member having a terminal opening, and a plurality of holes close to said terminal opening;
   a second treating member comprising a heating device connected to said outlet of said housing; and
   an air pump arranged in said housing to communicate said outlet and said inlet, wherein a vacuum is formed in said first treating member by driving said pump when said terminal opening in said first treating member is contacted onto and covers a location of the patient's body, wherein said lining is made of a ceramic material comprising at least one element selected from the group consisting of Fe, Zn, Cu, Cr, Mn, Co, In, Mo, and mixtures thereof.

2. An apparatus according to claim 1, wherein an insulating layer is arranged between said casing and said lining.

3. An apparatus according to claim 1, wherein said second treating member comprises a casing and a lining attached to said casing, and said heating device is electricity-heating wires wound in grooves on the outside of said lining, and the inner surface of said lining is coated with a medical infrared coating.

4. An apparatus for rebalancing chi in a patient, comprising a housing comprising an inlet and one outlet;

at least two first treating members connected to said inlet of said housing, each comprising a terminal opening and a plurality of holes close to said terminal opening; at least two second treating members connected to said outlet of said housing, each comprising a heating device; and an air pump arranged in said housing to communicate said outlet with said inlet, wherein a vacuum is formed in said first treating members by driving said pump when said first treating members are in contact with and cover a location of the patient's body, wherein said second treating member comprises a casing and a lining attached to said casing, and said heating device is electricity-heating wires wound in grooves on the outside of said lining, wherein said lining is made of a ceramic material that includes at least one element selected from the group consisting of Fe, Zn, Cu, Cr, Mn, Co, In, Mo, and mixtures thereof.

5. An apparatus according to claim 4, wherein an insulating layer is arranged between said casing and said lining.

6. An apparatus for rebalancing chi in a patient, comprising a housing comprising an inlet and one outlet;

at least two first treating members connected to said inlet of said housing, each comprising a terminal opening and a plurality of holes close to said terminal opening; at least two second treating members connected to said outlet of said housing, each comprising a heating device; and an air puma arranged in said housing to communicate said outlet with said inlet, wherein a vacuum is formed in said first treating members by driving said pump when said first treating members are in contact with and cover a location of the patient's body, wherein the inner surface of said lining is coated with a medical infrared coating.

* * * * *